US007432347B2

(12) United States Patent
Ohta et al.

(10) Patent No.: US 7,432,347 B2
(45) Date of Patent: *Oct. 7, 2008

(54) CYTOPLASMIC POLYHEDROSIS VIRUS POLYHEDRIN PROTEIN COMPLEX

(75) Inventors: Yoshimoto Ohta, Osaka (JP); Hajime Mori, Kyoto (JP); Keiko Ikeda, Kyoto (JP)

(73) Assignee: Protein Crystal Co., Ltd, Osaka-shi (JP)

( * ) Notice: Subject to any disclaimer, the term of this patent is extended or adjusted under 35 U.S.C. 154(b) by 315 days.

This patent is subject to a terminal disclaimer.

(21) Appl. No.: 10/415,096

(22) PCT Filed: Oct. 30, 2001

(86) PCT No.: PCT/JP01/09494

§ 371 (c)(1),
(2), (4) Date: Sep. 10, 2003

(87) PCT Pub. No.: WO02/36785

PCT Pub. Date: May 10, 2002

(65) Prior Publication Data

US 2004/0059091 A1 Mar. 25, 2004

(30) Foreign Application Priority Data

| Oct. 30, 2000 | (JP) | ............... 2000-330645 |
| Jan. 15, 2001 | (JP) | ............... 2001-006928 |
| Mar. 13, 2001 | (JP) | ............... 2001-071151 |

(51) Int. Cl.
*C07K 14/00* (2006.01)
*C12P 21/06* (2006.01)
*C12P 21/04* (2006.01)
*C12N 7/00* (2006.01)
*C12N 5/06* (2006.01)

(52) U.S. Cl. ............... 530/350; 435/69.1; 435/69.7; 435/235.1; 435/348

(58) Field of Classification Search ............... None
See application file for complete search history.

(56) References Cited

U.S. PATENT DOCUMENTS 4,870,023 A 9/1989 Fraser et al. ............... 435/320

FOREIGN PATENT DOCUMENTS

WO    WO 88/07082    9/1988

OTHER PUBLICATIONS

Payne et al. (1974) Intervirology 4:354-364.*
Mori et al. (1993) J Gen Virol 74:99-102.*
Branden et al. "Introduction to Protein Structure", Garland Publishing Inc., New York, 1991, p. 247.*
Wikipedia entry for "Cypovirus" http://en.wikipedia.org/wiki/Cypovirus, last visited on Jun. 14, 2006.*
Witkowski et al. (1999) Biochemistry 38:11643-11650.*
definition of "endogenous" at http://encarta.msn.com/, last viewed on Mar. 5, 2007.*
definition of "fuse" at http://encarta.msn.com/, last viewed on Mar. 7, 2007.*
Dai et al., Sci Sin [B]. 25:29-35, 1982.*
Hagiwara et al., J. Gen. Virol. 83:1477-1482, 2002.*
Mori et al., J. Biol. Chem. 282:1728917296, 2007.*
H. Mori et al.; J. Virol., 75(2), pp. 988-995, Jan. 2001. Cited in the int'l. search rpt.
T. Hong et al.; Proc. Natl. Acad. Sci. U.S.A., 94(8) pp. 4050-4055, Apr. 15, 1997. Cited in the int'l. search report.
J. E. Eason et al.; J. Virol., 72(7), pp. 6237-6243, Jul. 1998. Cited in the int'l. search rpt.
S. A. Monsma et al.; J. Virol., 70(7), pp. 4607-4616, Jul. 1996. Cited in the int'l. search rpt.
Tao Hong et al., "*N-terminal sequences from Autographa californica nuclear polyhedrosis virus envelope proteins ODV-E66 and ODV-E25 are sufficient to direct reporter proteins to the nuclear envelope, intranuclear microvesicles and the envelop of occlusion derived virus*", Proc. Natl. Acad. Sci. USA, vol. 94 (Apr. 1997), pp. 4050-4055.
Jane E. Eason et al., "*Effects of Substituting Granulin or a Granulin-Polyhedrin Chimera for Polyhedrin on Virion Occlusion and Polyhedral Morphology in Autographa californica Multinucleocapsid Nuclear Polyhedrosis Virus*," Journal of Virology, vol. 72, No. 7 (Jul. 1998), pp. 6237-6243.
Scott A. Monsma et al., "*The GP64 Envelope Fusion Protein Is an Essential Baculovirus Protein Required for Cell-to-Cell Transmission of Infection*," Journal of Virology, vol. 70, No. 7 (Jul. 1996), pp. 4607-4616.
Donald L. Jarvis et al., "*Requirements for Nuclear Localization and Supramolecular Assembly of a Baculovirus Polyhedrin Protein*," Virology, 185 (1991), pp. 795-810.

* cited by examiner

*Primary Examiner*—David J Steadman
(74) *Attorney, Agent, or Firm*—Westerman, Hattori, Daniels & Adrian, LLP.

(57) ABSTRACT

To provide a useful objective protein coated with a protective protein, a protein complex that is produced in cells and has a structure that the objective protein is occluded with the viral occlusion body protein. A protein complex having the structure that the objective protein is occluded with the viral occlusion body protein, produced in insect cells or plant cells, preferably produced by incorporation of the objective protein in the crystalline form during crystallization of polyhedron derived from polyhedrosis virus, preferably a protein complex in which the polyhedrin contributes to improvement of stability, or protection, or improvement of preservability, or combination thereof, of the objective protein.

Figure 1:
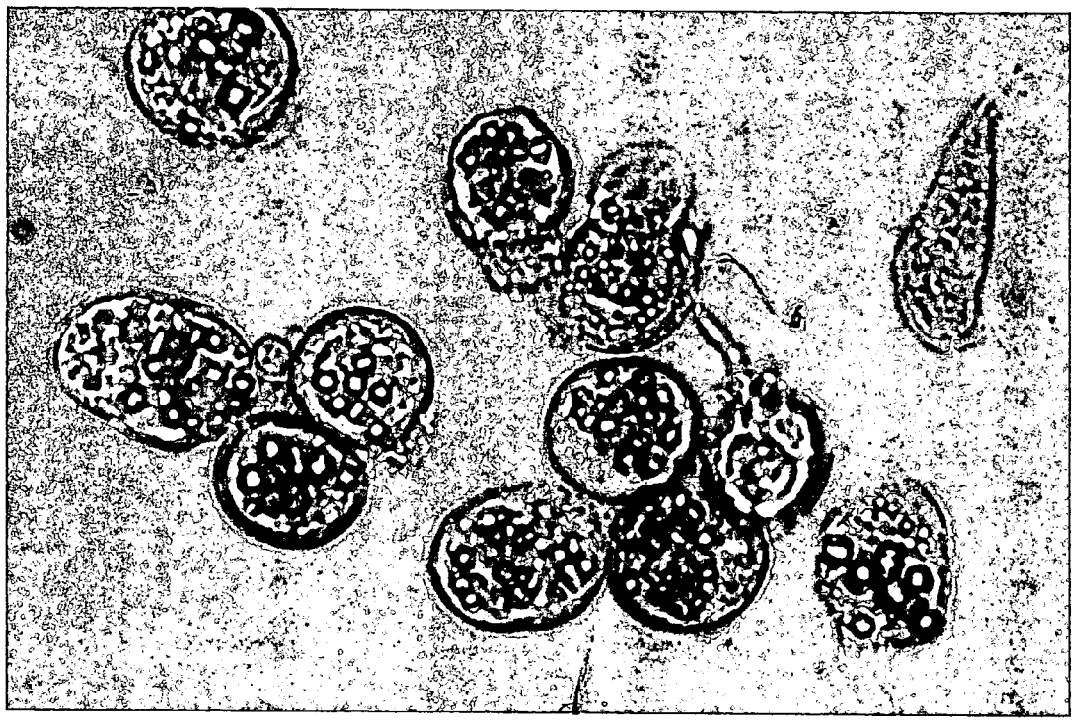
Figure 2:
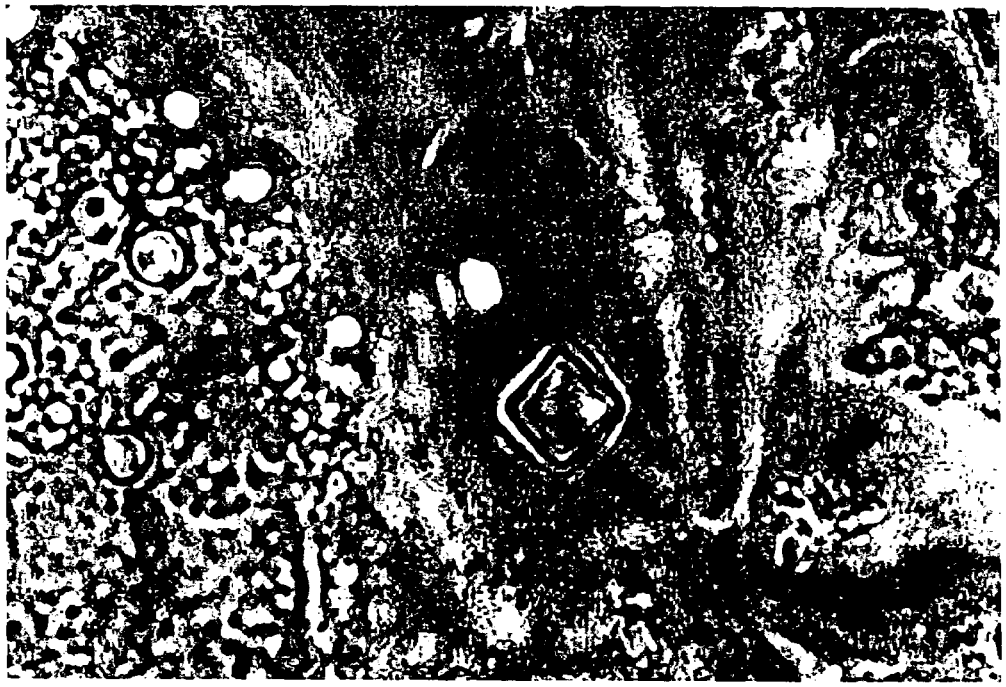
Figure 3:
Figure 3:
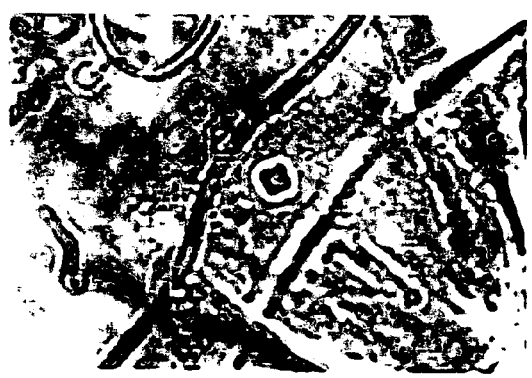
Figure 3:
Figure 3:

9 Claims, 6 Drawing Sheets before addition of alkali 20 seconds after addition 10 seconds after addition 40 seconds after addition

Fig.5

ΔKm^r  CaMV 35Spromoter  BmCPV polyhedrin   Hyg^r

Fig.6

Km^r   CaMV 35Spromoter   BmCPV VP3  GUS   Hyg^r

CYTOPLASMIC POLYHEDROSIS VIRUS POLYHEDRIN PROTEIN COMPLEX

FIELD OF THE INVENTION

This invention relates to protein complex and the method for producing various proteins, such as enzymes proteins, fluorescent proteins, and antibody, occluded with a viral occlusion body protein, in a pure state, preferably as crystalline forms, by utilizing cells, such as insect cells or plant cells.

BACKGROUND OF THE INVENTION

For occlusion of one protein with an another protein, an application of a solution of the protein onto a surface of the crystalline protein may be considered possible method, though in practical, it is extremely difficult to coat the crystalline protein with the solution of the protein without causing any dissolution. Coating for protection of useful proteins such as enzymes has rarely been performed.

Protection of proteins has conventionally known by attainment of a polymer, such as a polysaccharide or polyethylene glycol, covalently bonded to the protein. The method consists of reaction of the protein with the polymer to bind the functional groups in the protein, such as amino and carboxyl groups, under milder reaction conditions, where the binding site cannot be controlled. Therefore the method to protecting the protein cannot be applied to any kind of proteins.

Generally speaking, for preservation purpose of proteins, storage at lower temperatures and adding or mixing of a substance such as a polysaccharide and polyethylene glycol which is expected to stabilize the protein structure are performed. In any method, the protein to be protected will be dissolved together with the substance added and lose its stability when changes occur in the environment, especially when water comes in contact or temperature increases, or in case of dew condensation. Proteins will lose its function when degraded or ingested by microorganisms.

Polymeric proteins such as certain enzymes and antibody completely lose their functions when a part of the molecule is degraded by protease. They lose their functions quickly even when kept frozen due to weaker maintenance of their higer-order configuration.

To investigate the stability of an objective protein protected, it is necessary to isolate the protein and to check its individual function.

AS crystallization of a protein, smaller size crystals are generally obtained in research for the crystallization conditions, for example, by addition of a suitable metallic salt to a concentrated protein solution. There is no rule in crystallization, and therefore a number of crystallization conditions should be examined for each type of proteins to be crystallized.

DISCLOSURE OF THE INVENTION

In order to put useful proteins including enzymes to practical use, it is serious to maintain the function of individual proteins active. In general, proteins lose their functions such as catalytic activity when stored or allowed to stand at room temperature.

Therefore, for storage with the function maintained, proteins must be stored or kept at a low temperature, for example, in a refrigerator. A technique to maintain the function of proteins active is the means that can solve the subject matter to make the protein preservable and improve the stability; it is the subject matter to find a technique that can maintain the function of a protein at room temperature in a more stable way than with the conventional techniques for preservation of proteins.

It is an object of the invention to provide an useful objective protein, such as an enzyme, with its function maintained active as the result of improvement of stability, or protection, or improvement of preservability, or combination thereof.

It is an another object of the invention to maintain the function of an useful protein such as an enzyme for a long time by keeping in an aqueous solution. A technique required for this purpose is to coat the useful protein with a protective protein. The coating technique can protect the useful protein from the environmental influence, namely the technique can avoid the situation that may let the protein lose its function, such as dissolution of the protein in water, degradation or ingestion by microorganisms, etc.

It is an object of the invention to provide an useful protein, such as an enzyme, that has been coated with a protective protein. Proteins are biologically functional polymers having various chromophores or light-absorbing molecules, and thus their optical characteristics and electronic characteristics are expected to be useful. For making practical use of these characteristics, crystalline proteins rather than dried amorphous proteins are required.

Therefore it is the subject matter to produce such crystaline proteins. A technieque required first to solve the subject is the one that can provide such crystalline proteins. In general, crystallization of a protein is very difficult; then to produce easily crystalline proteins and to produce homogeneous crystals are the subjects to be solved by the technique.

It is an object of the invention to prepare the useful proteinsuch as an enzyme in the crystal form, more in detail, to produce the useful protein in the crystalline form by using theprotein produced in the crystalline form in cells as the protective protein for coating of the objective protein.

It is an another object of the invention to provide a method for easy production of the useful protein in the crystalline form by making use of the gene manipulation.

The technique to make use of the protein crystallized in cells is very effective in practical development of the protein as a novel material.

Cytoplasmic polyhedrosis virus forms polyhedra consisting of polyhedrin in the infected cells in the later stage of infection, and many virions are occluded in the polyhedra. It has been demonstrated that virions enter specifically into the polyhedra because of the specific relation between the viral occlusion body protein of virions and polyhedrin (J. Virol. 75, 988-995 (2001)).

It is an object of the invention to occlude the objective polymeric protein into the polyhedra and to improve the occlusion efficiency.

For this purpose, the gene coding for the viral occlusion body protein of cytoplasmic polyhedrosis virus is shortened to increase the size (molecular weight) of the protein that can be occluded in polyhedra and to occlude the objective protein efficiently in polyhedra.

To investigate a period that the function of the objective protein can be maintained by occlusion of the objective protein in polyhedra, an isolation of the objective protein from polyhedra was necessary. It is an object of the invention to make it possible to check at any time the function of the objective protein by occlusion of a protein that produces fluorescence or emission, such as a green fluorescent protein, together with the objective protein.

The subject matter of the invention is the protein complex produced in cells, more in detail, the protein complex produced in the form of particulates, with the objective protein occluded with the viral occlusion body protein.

The viral occlusion body protein contributes to improvement of stability, or protection, or improvement of preservability of the objective protein, or combination thereof, and therefore the invention relates to the protein complex produced in cells, more in detail, the protein complex produced in the form of particulates, with the objective protein occluded with the viral occlusion body protein where the viral occlusion body protein contributes to improvement of stability, or protection, or improvement of preservability of the objective protein, or combination thereof.

The protein complex is produced by incorporation of the objective protein in the crystal form during crystallization of the viral occlusion body protein, and therefore the invention relates to the protein complex produced in cells, more in detail the protein complex produced in the form of particulates, with the objective protein occluded with the viral occlusion body protein by incorporation of the objective protein in the crystal form during crystallization of the viral occlusion body protein, preferably the protein complex where the viral occlusion body protein contributes to improvement of stability, or protection, or improvement of preservability of the objective protein, or combination thereof.

The viral occlusion body protein is polyhedrin derived from polyhedrosis virus, and therefore the invention relates to the protein complex produced in cells with the objective protein occluded with polyhedrin, preferably the protein complex produced by incorporation of the objective protein in the crystalline form during crystallization of polyhedron derived from polyhedrosis virus, more in detail, the protein complex produced in the form of particulates, preferably the protein complex where polyhedrin contributes to improvement of stability, or protection, or improvement of preservability of the objective protein, or combination thereof.

The cells are those of insects or plants, and therefore the invention relates to the protein complex produced in cells of insects or plants with the objective protein occluded with polyhedrin, preferably the protein complex produced by incorporation of the objective protein in the crystal form during crystallization of polyhedrin derived from polyhedrosis virus, more in detail the protein complex produced in the form of particulates, preferably the protein complex where polyhedrin contributes to improvement of stability, or protection, or improvement of preservability of the objective protein, or combination thereof.

The objective protein is selected from a group consisting of enzymes, antigens, proteins bound to a biological material such as a different protein, proteins with photochemical characteristics, and functional proteins that donate or accept electrons, and therefore the invention relates to the protein complex produced in cells (in cells of insects or plants) with the objective protein occluded with polyhedrin, preferably the protein complex produced by incorporation of the objective protein, selected from a group consisting of enzymes, antigens, antibodies, proteins bound to a biological material such as a different protein, proteins with photochemical characteristics, and functional proteins that donate or accept electrons, in the crystal form during crystallization of polyhedrin derived from polyhedrosis virus, more in detail the protein complex produced in the form of particulates, preferably the protein complex where polyhedrin contributes to improvement of stability, or protection, or improvement of preservability of the objective protein, or combination thereof.

Another subject matter of the invention is the method for preparing a protein complex produced in cells with the objective protein occluded with the viral occlusion body protein.

Cells are those of insects or plants, and therefore the invention relates to the method for preparing a protein complex produced in cells of insects or plants with the objective protein occluded with the viral occlusion body protein.

After infection of cells with the virus vector integrated with the objective protein DNA together with the virus vector integrated with the viral occlusion body protein DNA, the cells are incubated to produce a protein complex with the objective protein occluded with the viral occlusion body protein, and therefore the invention relates to a method for preparing a protein complex with the objective protein occluded with the viral occlusion body protein in cells of insects or plants infected with the virus vector integrated with the objective protein DNA together with the virus vector integrated with the viral occlusion body protein DNA, and incubated to produce in the cells a protein complex with the objective protein occluded with the viral occlusion body protein.

The objective protein is selected from a group consisting of enzymes, antigens, proteins bound to a biological material such as a different protein, proteins with photochemical characteristics, and functional proteins that donate or accept electrons, and therefore the invention relates to a method for producing a protein complex with the objective protein, selected from a group consisting of enzymes, antigens, proteins bound to a biological material such as a different protein, proteins with photochemical characteristics, and functional proteins that donate or accept electrons, occluded with the viral occlusion body protein in cells of insects or plants, in more detail in the cells infected with the virus vector integrated with the objective protein DNA together with the virus vector integrated with the viral occlusion body protein DNA, and incubated to produce in the cells a protein complex with the objective protein occluded with the viral occlusion body protein.

In addition, the subject matter of the invention is a method for preparing a protein where a protein complex produced by one of the above-mentioned methods is collected so that an objective protein sample with high purity is obtained.

The patent or application file contains at least one drawing executed in color. Copies of this patent or patent application publication with color drawing(s) will be provided by the Office upon request and payment of the necessary fee.

BRIEF DESCRIPTION OF THE DRAWINGS

FIG. 1 is a microscopic picture of a crystal of the protein complex of the invention. FIG. 2 is a microscopic picture of the polyhedra formed in plant cells. FIG. 3 is a microscopic-picture illustrating dissolution of polyhedra under alkaline conditions. FIG. 4 is a graph showing the change in fluorescence of the protein complex crystal obtained in the Reference Example 2 with pH. FIG. 5 shows the vector p1G121-CP ($Kin^-$) for expression of polyhedrin. FIG. 6 shows the vector p1G121-VP3/GFP for expression of the VP3/GFP chimeric protein. FIG. 7 shows determination of fluorescence of the VP3/GFP chimeric protein contained in the polyhedra in plants.

BEST EMBODIMENTS OF THE INVENTION

<Objective Protein>

The objective protein occluded with the viral occlusion body protein is a so-called functional protein, preferably being in crystalline form.

The objective protein is exemplified by enzymes, antigens, antibodies, functional proteins with photochemical characteristics such as emission of fluorescence, high refractive index, photoelectric effects, and functional proteins that donate or accept electrons in electron transfer reaction, oxidation-reduction reaction, etc. More in detail, fluorescent proteins that emit fluorescence on irradiation of ultraviolet, enzymes having biologically catalytic action, antibodies, and physiologically active proteins including interferon and interleukin are the examples.

<Viral Occlusion Body Protein>

The viral occlusion body protein is, more in detail, the viral occlusion body protein encoded by virus which is polyhedrin encoded by insect cytoplasmic polyhedrosis virus. The viral occlusion body protein encoded by insect cytoplasmic polyhedrosis virus is exemplified by the viral occlusion body protein encoded by Bombyx mori polyhedrosis virus, BmCPV, (cytoplasmic polyhedrin).

The cytoplasmic polyhedrosis virus is classified under Cypovirus, Reoviridae. The virus is characterized in that it infects columnar cells of midgut epithelial cells of insects and produces large protein crystals called polyhedra in the cytoplasm of the infected cells. Polyhedra occlude many virions. Polyhedra consist of polyhedrin that is encoded by virus, expressed in the later stage of viral infection, and crystallized. One of the functions of polyhedra is to protect the infectivity of the virus itself from the outer environment in horizontal transmission of a viral disease. Namely, polyhedra are not dissolved at all in non-ionic or ionic surfactantsor an acidic or neutral solution. Even under irradiation of ultraviolet light, the occluded virus are kept unaffected. Because polyhedra are not dissolved by bacterial putrefaction, the virus in polyhedra are protected.

Another function of polyhedra is to bring the virus exactly to the objective site (cells in which virus can infect and proliferate). Namely, polyhedra ingested by an insect is dissolved by the strong alkaline digestive fluid of the insect, so that virions are released to infect the insect.

The viral genome is made of double-stranded RNA having ten segments (Segment 1 to Segment 10, designated as S1 to S10, respectively). Polyhedrin, a protein that constitutes of polyhedra, is encoded in the smallest segment S1O, having the molecular weight of 30 kDa. A virion of BmCPV comprises of five different proteins, VP1 (151 kDa), VP2 (142 kDa), VP3 (130 kDa), VP4 (67 kDa), and VP5 (33 kDa), respectively. A labeling experiment of BmCPV with isotope $^{125}$I has demonstrated that VP1 and VP3 are the proteins constituting of the outer layer of the virus(Lewandowski et.al., (1972) J. Virol. 10, 1053-1070) The result of an in vitro translation experiment using rabbit reticulocytes has suggested that the proteins constituting the outer layer of the virus, VP1 and VP3, are encoded in S1 and S4, respectively (McCrae nd Mertens(1983) in Double-Starnded RNA Viruses, Elsevier Biomedicals, 35-41).

Anaysis of S4 coding for VP3, a protein constituting the outer layer or BmCPV, revealed that S4 is composed of 3,259 bases, and has a large open reading frame (ORF) having the start codon at the $14^{th}$ and $16^{th}$ bases and the stop codon (TAA) at the 1,057 amino acid residues and the molecular weight of VP3 is estimated to be about 130 kDa.

The method for preparation of the virus vector integrated with the cytoplasmic polyhdrin molecule and the virus vector integrated with the functional protein molecule is illustrated for the case where Bombyx mori cytoplasmic polyhedrosis virus is used as the cytoplasmic polyhedrosis virus.

The virus vector integrated with the cytoplamic polyhedrin is prepared by, for Example, integration of the polyhedrin gene in the baculovirus vector derived from Autographa californica nucleopolyhedrovirus according to a prior art method [J. Gen. Virol., Vol. 74, pp. 99-102].

The virus vector integrated with the functional protein molecule is prepared by, for example, preparation of a chimeric gene coding for the fusion protein with the functional protein bound to the C-terminal of VP3, a protein constituting the outer layer of BombyxMori cytoplasmic polyhedrosis virus (BmCPV), followed by introduction into thabove-mentioned baculovirus vector derived from Autographa californica nucleopolyhedrovirus.

Then the two different virus vectors thus formed are allowed to infect insect tissue cells by inoculation of insect cells with the suspensions of the two different virus vectors at the same time, followed by keeping at room temperature for 0.5 to 3 hours to let virus adsorb sufficiently on cells, by removing of the virus suspension, by adding a culture medium containing fetal bovine calf serum, and by incubating at 20 to 300C for 2 to 10 days.

Then infected cells are separated from the culture and homogenized with cooling, and the solid matter containing polyhedra is collected by filtration or centrifugation from the homogenate to give the desired protein-embedded crystal. The protein-embedded crystal thus obtained can be purified, if necessary, by fractionation by the sucrose density gradient method and by washing with a buffer, etc.

In this manner, a protein-embedded crystal containing micro crystals of functional proteins is obtained at the weight ratio of 1/10 to 1/1000 of the cytoplasmic polyhedrin crystal.

In this procedure, the amino acid sequence of VP3, a protein constituting the outer layer of the cytoplasmic polyhedrosis virus, is inserted into the N-terminal or C-terminal of the functional protein, and the fusion protein is expressed by the baculovirus vector, where the fusion protein is occluded in the polyhedra when insect cells are infected together with the virus expressing the polyhedra of cytoplasmic polyhdrosis virus. Therefore it is necessary to ligate the cDNA coding for a constitutive protein of cytoplasmic polyhedrosis virus to a foreign protein gene so that the foreign protein expressed by baculovirus vector, namely the functional protein, may be integrated at the N-terminal or the C-terminal of the constitutive protein of cytoplasmic polyhedrosis virus. In this process, it is important to make in-frame the open reading frame coding for the constitutive protein and that for the protein of the foreign protein gene. In this way, a recombinant baculovirus is prepared that expresses a fusion protein consisting of a constitutive protein of cytoplasmic polyhedrosis virus and a foreign protein.

<Protein Complex in which the Objective Protein is Occluded with the Viral Occlusion Body Protein>

This is a protein-embedded crystal where the objective protein is dispersed in the viral occlusion body protein (cytoplasmic polyhedron crystal). This is produced as particulates by incorporation of the objective protein, preferably in the crystalline form, during crystallization of the viral occlusion body protein in cells. FIG. 1 is a microscopic picture of an example of the protein-embedded crystal of the invention, indicating that micro crystals of the functional protein are dispersed in the cytoplasmic polyhedrin crystal.

<Cells for Production of a Protein Complex>

Cells used for production of a protein complex are not particularly specified as far as they are susceptible to viral infection.

Cells may be insects or insect cells, or plants or plant cells.

<Protein-embedded Crystal Produced in an Insect>

A protein-embedded crystal can be produced by, for example, separate preparation of a virus vector integrated with the polyhedron molecule and a virus vector integrated with a functional protein, simultaneous infection of insect tissue cells with the two virus vectors to produce polyhedra in the insect cells infected with the two viruses, and separation of the polyhedra as crystals. Namely, simultaneous infection with the cytoplasmic polyhedrosis virus and the virus coding for the functional protein can produce at a stroke polyhedrin crystals dispersed with micro crystals of the functional protein.

Insects used for infection with the two different virus vectors are not specified as far as the cells are susceptible to viral infection, and those of Lepidoptera, particularly those classified under Geometridae, Salurniidae, Bombycidae, Arctiidae, and Noetuidae are generally used. Usually *Bombyx mori* L., Antheraea assamensis Helfer, Peridroma sp., Leucania unipunctata Howorth, and the like are used because of their easiness in availability and handling.

A VP3/GFP chimeric gene that lacks the restriction enzyme site Xbal at the region between the $1358^{th}$ and the $2711^{th}$ of S4 coding for VP3 (VP3(Xbal)/GFP) was prepared. Then the gene was introduced into the baculovirus vector derived from *Autographa californica* nucleopolyhedrovirus (AcNPV), and the VP3(Xbal)-GFP fusion protein was expressed in IPLB-Sf21-AE (Sf21) derived from cells of an insect *Spodoptera frugiperda*. For production of cubic polyhedra, the recombinant AcNPV (AcCP-H) integrated with the cytoplasmic polyhedrin gene was used at the same time to inoculate the Sf21 cells (Mori et al. (1993) J. Gen. Virol. 74, 99-102). Polyhedra was purified from the Sf21 cells infected with the two different viruses, and it was examined under green fluorescence whether the fusion protein was occluded in the polyhedra and released on dissolution of the polyhedra under alkaline conditions. The fusion protein consisting of VP3(Xbal) and GFP was released when polyhedra was dissolved, as was the fusion protein consisting of VP3 and GFP, indicating that the fusion protein had been incorporated specifically in the polyhedra. This demonstrated that VP3 can be shortened in the procedure for incorporation of the objective protein in particulates called polyhedra and in the procedure for preparation of particulates with the objective protein occluded with a protein called polyhedrin.

<Production of Various Functional Protein Crystals in Pure State>

Cytoplasmic polyhedrin crystals in protein-embedded crystals are soluble in an alkaline solution, whereas functional protein micro crystals occluded therein are stable to alkali. Therefore various functional protein crystals can be produced in the pure state by making use of such protein-embedded crystals.

This invention provides a method for production of pure, functional protein crystals characterized in that insect cells are infected with the virus vector integrated with a functional protein DNA together with the virus vector integrated with the cytoplasmic polyhedrin DNA of the cytoplasmic polyhedrosis virus and then cultured to produce protein-embedded crystals consisting of cytoplasmic polyhedrin crystals with the functional protein crystals occluded, followed by dissolution of the protein-embedded crystals in an alkaline aqueous solution and isolation and harvesting of the functional protein crystal from the solution.

In the concrete, when an alkali, for example a sodium hydroxide solution, is added to the polyhedra containing a functional protein to pH 8.0, preferably to pH 8.5 to 11 .0, the protein-embedded crystals are dissolved but only the cytoplasmic polyhedrin is precipitated when the solution is made neutral again. Therefore when the precipitates and the cell debris are removed by centrifugation or filtration, a solution containing only the functional protein is obtained.

The buffer to be used is a buffer used for usual gene manipulation, such as acetate buffer or phosphate buffer. The treatment is made at room temperature, namely in the range of 5 to 30 CC, and warming is permitted if necessary as far as it does not damage the functional protein, and gentle stirring or shaking is also permitted if necessary to promote dissolution. Then the buffer containing only the functional protein is treated with a conventional technique for harvesting of protein crystals from the solution, such as concentration, freeze-drying, or fractional salting-out, so that the functional protein crystals are recovered in the pure state from the above-mentioned solution.

The invention is explained by the protein-embedded crystals produced in plants as an example.

Protein-embedded crystals produced in plants of the invention consist of two different crystals, the viral occlusion body protein crystals and the objective protein micro crystals, and the objective protein micro crystals are dispersed in the viral occlusion body protein crystals.

Analysis based on the database of the amino acid sequence of VP3, one of the outer layer proteins of Bombyx marl cytoplasmic polyhedrosis virus (BmCPV), revealed that the protein shows a high homology with the virus capsid protein of Oryzavirus classified under Reoviridae and with that of plant reovirus classified under Fijivirus [Ikeda et al., (2001) Journal of Virology 75, 988-995]. This allowed us to expect that the virus capsid protein of BmCPV or polyhedrin, when expressed in plants, will be processed into a protein having a function similar to that in insect cells.

<Expression of VP3IGFP Polyhedra in Plants>

Then the green fluorescent protein (GFP) as a functional protein was ligated to the C-terminal of VP3 for preparation of a chimeric gene coding for the fusion protein consisting of VP3 and GFP (VP3/GFP). By using the plasmid pAcVP3/GFP containing the VP3/GFP-chimeric gene and the plant expression vector Ti plasmid pIG 121, the Ti plasmid vector pIG 121-VP3/GFP having the VP3/GFP chimeric gene downstream of the CaMV 35S promoter was constructed in 3 steps. Separately, the polyhedrin gene was excised as the Kpn I-Sac I region from pBS(KS)-H and inserted downstream of the GaMy 35S promoter of pIG 121 to construct the vector pIG 121-H. Into the plant (potato or belladonna) where expression had been confirmed after introduction of pIG 121-H by the method of agrobacterium, pIG 121-VP3/GFP was introduced to obtain a transformed plant having both genes. It was confirmed with the Western blot analysis that polyhedrin and the GFP protein had been produced, and formation of polyhedra was confirmed by microscopic examination (FIG. 2). Under the microscope, the plant tissue was treated with an alkali, and it was observed along time that polyhedra was dissolved in a very short time; thus the characteristic of polyhedra that it is dissolved under alkaline conditions could be confirmed (FIG. 3). It was also observed that green fluorescence due to the VP3/GFP chimeric protein released from polyhedra was emitted, though not so evidently as with Bombyx mon cells because of interference by natural fluorescence of the plant itself. Thus we have developed a method for incorporation of the objective protein into particulates called polyhedra in a transgenic plant containing the expression system of the polyhedrin gene and the VP3/GFP chimeric gene, and a method for production of particulates containing the objective protein occluded with a protein called polyhedrin.

<Detection and Purification of Interacting Protein by Making Use of Recombinant Polyhedra>

The function and the integrity of cells are based on the interaction among various polymeric substances (between a protein and a different protein, between DNA and a protein). For detection of these interacting substances, the far-western blot analysis and the two-hybrid system method have been developed. With these methods, the interacting molecules are detected indirectly based on the reaction with an antibody or the activity of the reporter gene, and therefore it is generally difficult to detect and purify in one step the interacting protein as it is in cells. The method of the invention making use of the recombinant polyhedra aims to remove such restriction.

Now we assume a pair of proteins A and B that interact with each other. A recombinant polyhedra is produced by using the gene coding for the protein A and isolated. A part of the protein A synthesized is bound to the surface of polyhedra. The polyhedra is mixed in the cell extract containing the protein B that interacts with the protein A and allowed to react for a suitable time, followed by separation of polyhedra by centrifugation. Thus the protein B bound to the protein A on the surface of polyhedra can be purified in one step from many coexisting proteins. This procedure is able to detect and purify the protein B as it has been extracted from cells, because the procedure requires no operations such as electrophoresis, blotting on the membrane, and the like. If the protein A is a protein taking part in gene expression, the procedure can be utilized as an improved south-western blotting to detect the interaction between DNA and the protein by using a genome DNA fragment as the protein B.

Particulates with the objective protein occluded are produced in plants according to the above-mentioned procedure, and the particulates are collected so that the objective protein of a high purity can be recovered.

For stabilization of an unstable functional protein crystal by occlusion in a stable protein crystal, cytoplasmic polyhedrosis virus, which infects the columnar cells of the insect midgut epithelium and produces large protein crystals called polyhedra in the cytoplasm of the infected cells, can be used to form protein-embedded crystals with various functional proteins dispersed and occluded in the above-mentioned polyhedrosis virus protein crystals.

By incorporation of a particular protein in polyhedra derived from cytoplasmic polyhedrosis virus (cytoplasmic polyhedra), it is able to bind a biological material such as a different protein to the protein, and the biological material bound to cytoplasmic polyhedra can be recovered.

A common practice for recovery of a particular protein alone is that a specific antibody to the protein is prepared first and the protein is recovered as a precipitate or the like by making use of the antigen-antibody reaction between the protein and the antibody. However with this method the protein to be isolated must be obtained in a highly purified state, and moreover, the antibody to the protein must be prepared. On the other hand, when a particular protein is incorporated in cytoplasmic polyhedra and then added to a crude sample such as a cell extract, the protein distributed on the surface of cytoplasmic polyhedra is bound to the biological material present 24 in the crude sample. Cytoplasmic polyhedra can be harvested easily by centrifugation or the like, and therefore the biological material bound to cytoplasmic polyhedra can be recovered. A particular protein can be incorporated in polyhedra by using the gene coding for the protein if any. Therefore the function of a protein encoded by an unknown gene that has been obtained during genome analysis can be investigated.

For preparation of protein crystals required for X-ray analysis, a crystal-like protein is incorporated in cytoplasmic polyhedra. Then the polyhedra is subjected to X-ray analysis, and the blank cytoplasmic polyhedra which contains no foreign material is also subjected to X-ray analysis. The analytical data of the protein incorporated in cytoplasmic polyhedra is obtained by comparison of the results of two analyses.

Incorporation of a crystal-like protein in cytoplasmic polyhedra can produce crystals of the protein by using the resultant cytoplasmic polyhedra as the nucleus.

The stereochemical configuration of a protein is investigated with the X-ray analysis. For this analysis, crystals of the protein are needed. However for crystallization of a protein it is required to obtain a highly-purified protein and to find crystallization conditions appropriate for the properties of the protein. Generally this process requires about a half year or a longer time. It is not infrequent that certain proteins cannot be crystallized. However because a crystal-like protein can be incorporated in 2-2 cytoplasmic polyhedra, the protein incorporated in cytoplasmic polyhedra can directly be analyzed with X-ray or crystals can be grown with the cytoplasmic polyhedra as the nucleus. In the latter case the cytoplasmic polyhedra is an important tool for preparation of crystals of a protein, because protein will be crystallized easily in the presence of a nucleus.

If a protein is incorporated in cytoplasmic polyhedra after fusion with a green fluorescent protein, the state of the protein in the polyhedra can easily be examined for example by use of emission. Whether the objective protein has been incorporated in cytoplasmic polyhedra is examined by collection of polyhedra, dissolution of polyhedra in an alkaline solution (pH 11), and isolation of the protein incorporated. However, if a protein is incorporated together with an emitting protein such as a green fluorescent protein in cytoplasmic polyhedra, incorporation of the objective protein can be confirmed by use of the emission of cytoplasmic polyhedra. For practical use of a useful protein such as an enzyme, maintenance of the function of the protein has been an important problem. Namely, a protein, when stored or allowed to stand at room temperature, generally loses its function, for example the catalytic activity of an enzyme, and therefore for storage of a protein with its function maintained, it should be stored or allowed to stand at a low temperature for example in a refrigerator. The technique for maintenance of the function is the mean that can solve the subject of improvement of preservability and stability of the protein, and it is the subject matter that a protein can be stored at room temperature with the function of the protein maintained more persistently than with the conventional means for storage of proteins.

This invention can provide a useful protein such as an enzyme with its function maintained by improvement of stability, or protection, or improvement of preservability of the protein, or combination thereof.

It is another subject matter that a useful protein such as an enzyme is stored in the form of an aqueous solution so that the function may be maintained for a long time. This requires a technique for coating the useful protein with a protective protein. The coating technique is able to avoid influence of the outer environment on the useful protein, that is, the situation that makes the useful protein lose its function, for example, dissolution of the protein in moisture, or degradation or ingestion by microorganisms.

This invention can provide a useful objective protein such as an enzyme that is coated with a protective protein.

Proteins are functional biological polymers which may have various chromophores or light-absorbing molecules, and their optical characteristics and electronic characteristics are expected to be practically useful. For such practical application, not amorphous dry proteins but crystal-like proteins are needed, and therefore production of crystal-like proteins is a subject matter. For this, a technique to provide crystal-like proteins is required. In general, crystallization of a protein is extremely difficult, and the subject matter that is to be solved with the technique is to produce readily crystal-like proteins and to prepare homogeneous crystals.

This invention can provide a useful objective protein such as an enzyme as a crystal, more in detail, the invention can e provide a useful objective protein such as an enzyme as a crystal by using the protein produced as crystals in cells as the protective protein for coating of the objective protein.

This invention can provide also a method for easy preparation of a useful objective protein such as an enzyme as a crystal by making use of the gene manipulation.

The technique that utilizes the protein produced as crystals in cells is very effective for development of use of a protein as a novel material. However there is a risk of contamination of polyhedra by baculovirus when polyhedra is prepared in insect cells and when the objective protein is incorporated in polyhedra by using the baculovirus vector, the baculovirus expression vector system, as have been so far. Also when polyhedra is purified from insect cells, there is a risk of contamination of the sample by baculovirus. When a large amount of polyhedra that has incorporated the objective protein is necessary, it is required to proliferate much insect cells by some means and to infect the cells with the recombinant baculovirus vector, which entails enormous costs.

Because it is possible to allow plants to produce polyhedra, the above-mentioned risk of viral contamination and the problem in cost can be solved by incorporation of the objective protein in plant polyhedra.

The viral occlusion body protein of virus such as cytoplasmic polyhedrosis virus (polyhedrin) in this invention produces particulates called polyhedra as a result of crystallization in cells. During the process of crystallization, the objective protein that is occluded in the particulates is also incorporated as crystals. Therefore the objective protein incorporated in the particulates can be used as the nucleus for crystallization necessary for production of crystals of the objective protein.

The details of the invention are illustrated in the Examples. The invention is not restricted at all by the Examples.

EXAMPLES

<<Virus and Cells>>

The H strain of *Bombyx mori* cytoplasmic polyhedrosis virus (BmCPV) forms cubic polyhedra in cytoplasm. The recombinant virus (AcC P-H) constructed to express only the polyhedrin of the H strain was used. Insect cells used were subcultures of IPLB-Sf21-AE derived from *Spodoptera Frugiperda* (Sf21) in the TC-100 (GIBCO BRL) medium containing 10% fetal bovine calf serum.

(1) Synthesis of cDNA

The double stranded RNA was extracted from BmCPV, and the fourth segment (abbreviated as S4 hereinafter) was isolated by using a low temperature melting agarose gel [manufactured by FMC Co., trade name "GTG"]. Then two different primers were synthesized according to the prior art method ["Virology", Vol.181, pp.749-755 (1991)], with the Sequence No.3 in the sequence list (the $5^{th}$ to $12^{th}$ from the left terminal is the Not1 site) for the (+) strand and Sequence No.4 in the sequence list (the $5^{th}$ to $10^{th}$ from the left terminal is the BamH1 site) for the (−) strand based on the terminal sequences of S4. Then these primers were used for preparation of cDNA of S4 with the Timesever cDNA Synthesis Kit (manufactured by Amasham Pharmacia Biotech Co.), followed by PCR-amplification by using Ex Taq polymerase (manufactured by Takara Co.). The amplified PCR product was digested with a restriction enzyme that restricts selectively at the Not1 site (called Not1 restriction enzyme hereinafter) and a restriction enzyme that restricts selectively at the BamH1 site (called BamH1 restriction enzyme hereinafter).

(2) Construction of Recombinant Baculovirus (I)

The segments obtained by digestion of cDNA of S4 with the restriction enzymes Not1 and BamH1 were integrated in the Not1-BamH1 site of the baculovirus transfer vector pVL1392 (manufactured by PHARMINGEN Co.) to construct the recombinant transfer vector pAcVP3. Then pAcVP3 was digested with restriction enzymes that restrict selectively at the site Bglll on the $2964^{th}$ and the site Sail on the $2999^{th}$, respectively, of the nucleotide sequence of S4, followed by integration at the Bglll-Sall site of the vector pEGFPN2 (manufactured by CLONTECH Co.) that expresses a fusion protein with the green fluorescent protein (abbreviated as GFP hereinafter).

This vector was then digested with the restriction enzyme Not1 followed by integration at the Not1 site of the baculovirus transfer vector (pVL1392), to construct the recombinant transfer vector (pAcVP3/GFP). Separately, pEGFPN2 was digested with the restriction enzyme BamH1 and the restriction enzyme Not1 , followed by integration at theBamH1-Not1 site of the baculovirus transfer vector (pVL1392) 2 (manufactured by PHARMINGEN Co.), to construct the recombinant transfer vector (pAcGFP) that expresses only GFP. These 3 different recombinant transfer vectors thus constructed, 5 µg each, were used for transfection of cultured insect cells Sf21 together with 0.5 µg of filamentous Baculogold Baculovirus DNA (manufactured by PHARMINGEN Co.) according to the lipofectin method. Then plaque purification was performed to give respective recombinant viruses, AcVP3, AcVP3/GFP, and AcGFP.

(3) Construction of Recombinant Baculovirus (2)

The segments obtained by digestion of cDNA of S4 with the restriction enzymes Not1 and BamH1 were integrated into the Not1-BamH1 site of the baculovirus transfer vector pVL1392 (manufactured by PHARMINGEN Co.) to construct the recombinant transfer vector pAcVP3. Then pAcVP3 was digested with the restriction enzyme Xbal (present at the region from $1,358^{th}$ to $1,363^{rd}$ and from $2711^{th}$ to $2,716^{th}$ of the nucleotide sequence of S4), and the recombinant transfer vector pAcVP3(Xbal) was constructed by self-ligation. This vector pAcVP3(Xbal) was then digested with the restriction enzymes Bglll and Sall (present in the region from the $2,964^{th}$ to $2,999^{th}$ of the nucleotide sequence of S4), followed by integration at the Bglll -Sall site of the vector pEGFPN2 that expresses a fusion protein with green fluorescent protein; GFP) (manufactured by CLONTECH). Digestion with Not1 and integration at the not1 site of the baculovirus transfer vector pVL1392 were performed to construct the recombinant transfer vector pAcVP3(Xbal)/GFP. The recombinant transfer vector thus constructed, 5p g, was used for transfection of cultured insect cells Sf21 together with 0.5 p g of filamentous Baculogold Baculovirus DNA (manufactured by PHARMINGEN Co.) according to the lipofectin method. Then plaque purification was performed to give the recombinant virus AcVP3(XbaI)/GFP.

<<Expression of the Recombinant Protein in Sf21 Cells>>

The recombinant virus was allowed to infect Sf21 cells at 20 p.fu./cell ($1 \times 10^6$ cells/35 mm Petri-dish). Double infection with two different viruses, for example with AcVP3/GFP and AcCP-H or with AcVP3(XbaI)/GFP and AcCP-H, was performed at 10 p.f.u./cell. After virus was allowed to adsorb to cells at room temperature for I hour, the virus solution was removed, and 2 ml of TC-100 containing 10% fetal bovine calf serum was added, followed by incubation at 27° C. for 4 days. The infected cells were used for Western blotting or measurement of fluorescence.

<<Purification of Polyhedra>>

The BmCPV H-strain-derived recombinant baculovirus AcCP-H that produces cubic polyhedra (Mori et al. (1993) J. Gen. Virol. 74, 99-102) and AcVP3/GFP or AcVP3(XbaI)/GFP were allowed to infect Sf21 cells ($1 \times 10^8$ cells), and cubic polyhedra was harvested from the infected cells on the $4^{th}$ day. After washing with PBS (20 mM $NaH_2PO_4$, 20 mM $Na_2HPO_4$, 150 mM NaCl, pH7.2), polyhedra was homogenized in ice with a homogenizer. The homogenate was washed with 1% Tween 20, and polyhedra was harvested by centrifugation. Then centrifugation with the sucrose density gradient from I 0.5M to 2.2M at 50,000×g for 45 minutes was performed to separate the fraction of polyhedra. The separated sample was washed with PBS, followed by centrifugation at 50,000×g for 10 minutes, to collect purified polyhedra.

<<Expression of GFP-VP3 Fusion Protein>>

Figure 4:
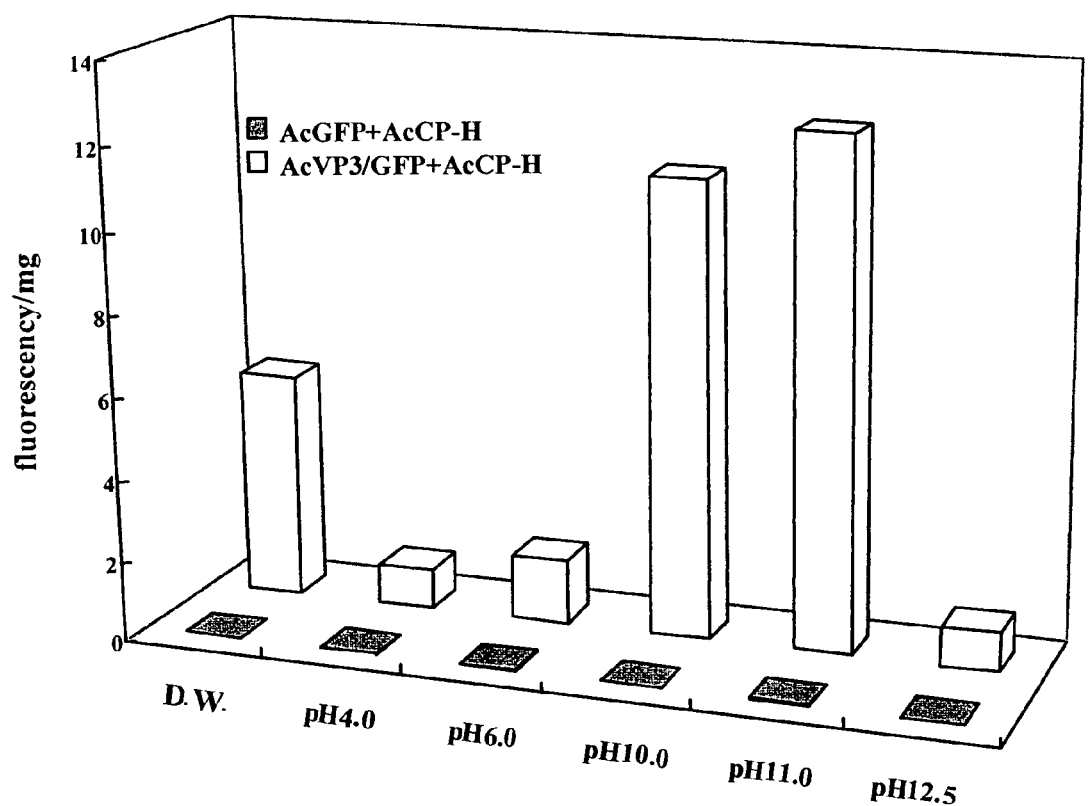

Polyhedra was purified from cells double-infected with AcVP3/GFP and AcCP-H or with AcVP3(XbaI)/GFP and AcCP-H, and suspended in the acetate buffer (pH4.0) to deactivate GFP without dissolving polyhedra. Then green fluorescence was measured which became dissolved from polyhedra when pH was elevated. Green fluorescence showed no change at pH 10.0 or a lower pH, but polyhedra was dissolved and green fluorescence was confirmed when pH exceeded 10.0 (FIG. 4). This suggested that the VP3-GFP fusion protein was occluded in polyhedra and dissolved when polyhedra was dissolved. Also polyhedra purified from cells double-infected with AcVP3(XbaI)/GFP and AcCP-H was suspended in the acetate buffer (pH4.0) to deactivate GFP without dissolving polyhedra, and green fluorescence from polyhedra was measured while pH was elevated. Green fluorescence showed no change at pH 10.0 or a lower pH, but polyhedra was dissolved and green fluorescence was confirmed again when pH exceeded 10.0 (FIG. 4).

Namely, it has been demonstrated that polyhedrin of BmCPV and VP3 identify each other through their specific interaction, that the VP3-GFP fusion protein (one of the Examples of objective proteins of this invention) is occluded in particulates called polyhedra, and that even when VP3 has lost its latter half or more (VP3(XbaI)), VP3(XbaI)/GFP is efficiently occluded in polyhedra.

Reference Example 1 cDNA synthesized in (1) was cloned in the plasmid pBluescript11 [manufactured by Stratagene Co.], and the deletion mutants for each of 5 clones obtained were formed by using the Deletion Kit for kilo-sequence (manufactured by Takara Co.).

The ABIPRISM terminator cycle sequencing kit and the 373A automated sequencer manufactured by PE Applied Biosystems Co. were used for analysis of the nucleotide sequence; it was demonstrated that S4 of BmCPV is 3,259-bases long as shown in the Sequence No.1 in the sequence list, which contains a large open reading frame (ORF) having a start codon from the $14^{th}$ to $16^{th}$ (ATG) and the stop codon from the $3,185^{th}$ to $3,187^{th}$ (TAA). This ORF consists of 1,057 amino acid residues (Sequence No.2), of which molecular weight was estimated to be about 130 kDa. Western blot analysis revealed that there is a band corresponding to about 130 kDa also in purified VP3 of virion. The SDS-PAGE of non-infected cells, AcNPV-infected cells and AcVP3-infected cells showed a new band corresponding to the molecular weight of about 130 kDa, and the western blot analysis showed that the antibody reacted. Thus VP3 was confirmed to have been encoded in S4.

Reference Example 2

It is known that GFP is stable at a pH between 5 and 12, and polyhedra is dissolved at a pH exceeding 10.0. Then fluorescence from GFP was measured before and after dissolution of polyhedra to determine whether VP3 was occluded in polyhedra. Polyhedra, after purification, was suspended in 1 ml each of distilled water, 50 mM acetate buffer (pH4.0), and 5 mM carbonate-bicarbonate buffer (pH 11.0). The pH of the suspension in the acetate buffer was gradually elevated by addition of the 5 mol/$m^3$ NaOH solution, and the suspension was incubated at 30° C. for 30 minutes when pH became 6.0, 10.0, and 12.5, and the fluorescence of GFP was excited at 475 nm and measured at 51O nm by the fluorometer (manufactured by Hitachi Seisakusho, Product code F-2000). The result is illustrated in the graph in FIG. 4.

Single infection with AcVP3/GFP and double infection with AcVP3/GFP and AcCP-H were performed in 35-mm Petri dishes, and emission of fluorescence from GEP was confirmed with the Olympus photomicroscope on the $4^{th}$ day after infection.

Reference Example 3

When cells double-infected with AcVP3/GFP and AcCP-H were examined microscopically, an intense green fluorescence was confirmed along the border of polyhedra of BmCPV. However green fluorescence was noted all over the cytoplasm in cells infected with AcVP3/GFP alone. Therefore, it was supposed that there might be some interaction between polyhedrin of BmCPV and VP3, though it was still unknown whether VP3 was occluded in polyhedra of BmCPV.

Then polyhedra was purified from cells double-infected with AcVP3/GFP and AcCP-H, and suspended in the acetate buffer (pH4.0) to deactivate GFP without dissolving polyhedra, and green fluorescence was measured that was dissolved from polyhedra by elevating pH. Green fluorescence was not noted at pH 10.0 or a lower pH whereas polyhedra was dissolved and green fluorescence was confirmed when pH exceeded 10.0. In contrast, no green fluorescence was detected in a similar measurement after double infection with AcGFP and AcCP-H. These results suggested that the VP3-GFP fusion protein was occluded in polyhedra and became dissolved along with dissolution of polyhedra. Namely, it has been demonstrated that polyhedrin of BmCPV and VP3 identify each other through their specific interaction, and the VP3-GFP fusion protein is occluded in particulates called polyhedra.

Virus and Cells

The H strain of *Bombyx mori* cytoplasmic polyhedrosis virus (BmCPV) forms cubic polyhedra in cytoplasm. The recombinant virus AcCP-H constructed to express only the polyhedrin of the H strain was used. Insect cells used were subcultures of IPLB-Sf21-AE derived from *Spodoptera Frugiperda* (Sf21) in the TC-100 (GIBCO BRL) medium containing 10% fetal bovine calf serum.

Synthesis of cDNA

The double-stranded RNA was extracted from BmCPV, and the fourth segment (S4) was isolated by using a low temperature melting agarose gel (FMC). Then two different primers were synthesized based on the terminal sequences of S4 reported by Kuchino et al. [Kuchino et al. (1991) Virology, 181, 749-755];

5'GATCGCGGCCGCAGTAATTTCCACCATG3' (SEQ ID NO:3)(the region underlined is the Not1 site) for the (+) strand and 5'GATCGGATCCGGCTAACGTTTCC3' (SEQ ID NO:4) (the region underlined is the BamH1 site) for the (−) strand. Then these primers were used for preparation of cDNA of S4 with the Timesever cDNA Synthesis Kit (Amasham Pharmacia Biotech). The cDNA thus synthesized was amplified by PCR using Ex Taq polymerase (TAKARA). The amplified PCR product was digested with the restriction enzymes Not1 and BamH1. The fragments were integrated into the Not1-BamH1 site of pBlueScript II (SK+) (STRATAGENE), and then transformed by using *E.coli* JMIO9(TOYOBO), and 5 clones were used for analysis of nucleotide sequence.

Analysis of Nucleotide Sequence

Deletion mutants for each of 5 clones having the full length of S4 were obtained by using the Deletion Kit for kilo-sequence (TAKARA). The nucleotide sequence was analyzed by using the ABIPRISM terminator cycle sequencing kit (PE Applied Biosystems) and the 373A automated sequencer of PE Applied Biosystems.

Experimental Example 2

Confirmation of Formation of Polyhedra by Plants

Figure 7:
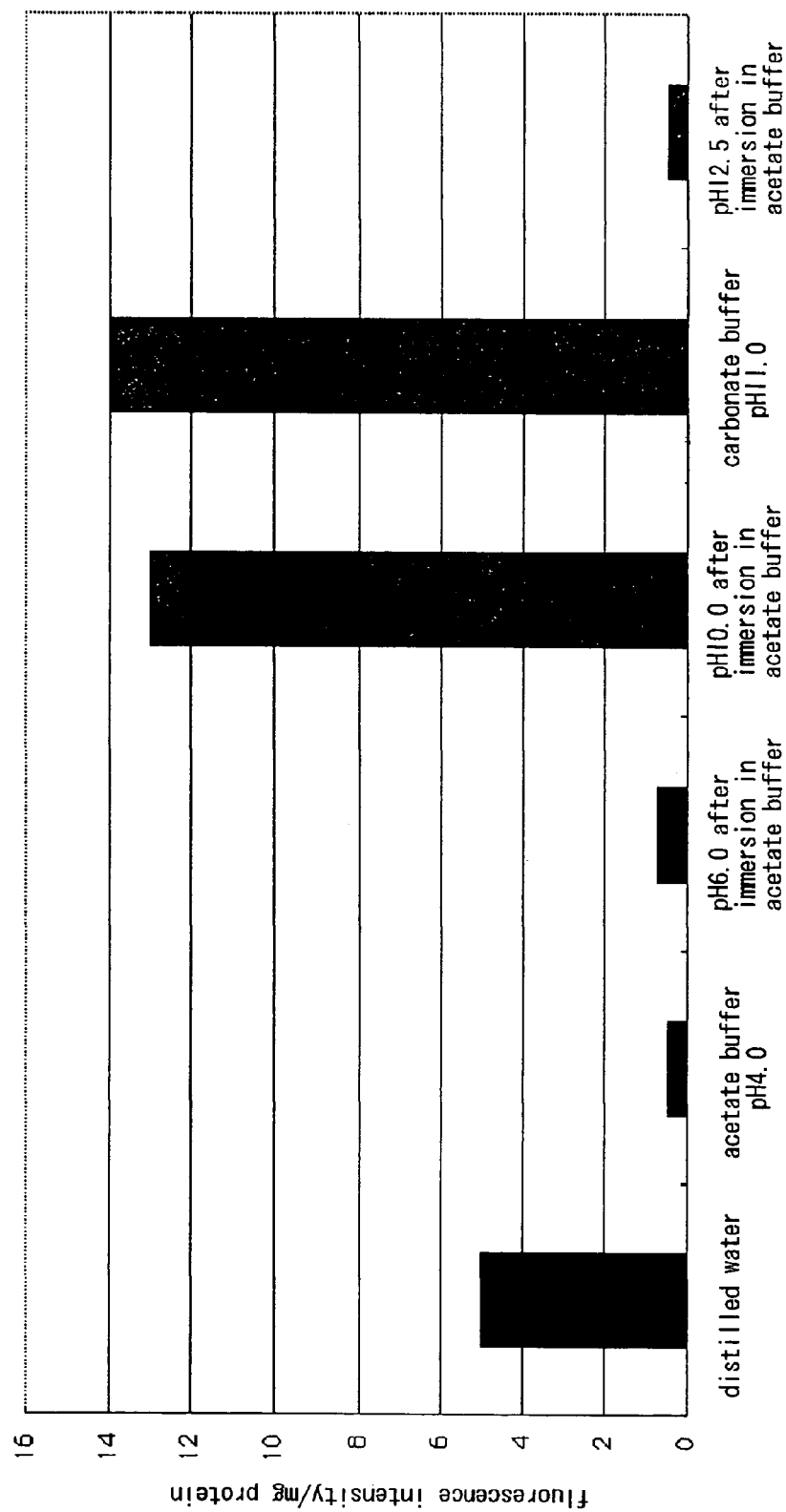

For demonstration of formation of polyhedra within plant cells as a result of expression of the polyhedrin gene, the GUS gene of the plasmid vector pIG121was exchanged with the polyhedrin gene to prepare pIG121-CP(FIG. 5). First, PIG121was digested with the restriction enzyme Sal1 to remove the GUS gene, and the polyhedron gene of BmCPV was inserted instead. By making use of the fact that the resultant plasmid has two different antibiotics (kanamycin and hygromycin)-resistant genes, it is possible to confirm selection of transformed cells, mRNA, expression of polyhedrin, and formation of polyhedra. However, as described below, it was necessary to insert additionally the VP3/GFP chimeric gene into the transformed plant cells integrated with the polyhedrin gene, and for easier screening, the major part of the kanamycin-resistant gene was removed by digestion with the restriction enzyme Sph1 to prepare the plasmid pIG121-CP ($Km^-$), which was used. The resultant transformed plant was hygromycin-resistant and kanamycin-sensitive. This transformed plant was found to have formed cubic polyhedra similar to that formed in insect cells by using the baculovirus vector.

Expression of VP3-GFP in Plants

By exchange of the VP3-GFP chimeric gene with the GUS gene of pIG121, pIG121-VP3/GFP was prepared (FIG. 6). Namely, pIG121 was digested with the restriction enzyme Sail to remove the GUS gene, and the VP3-GFP chimeric gene was inserted instead. By making use of the fact that the resultant plasmid has two different antibiotics (kanamycin and hygromycin)-resistant genes, it is possible to confirm selection of transformed cells, mRNA, expression of the chimeric protein, and ability of GFP to emit green fluorescence. When the resultant transformed plant cells were irradiated with ultraviolet light, emission of green fluorescence was confirmed.

Expression of Both Polyhedrin Gene and VP3/GFP Chimeric Gene

Into the transformed plant cells integrated with the polyhedron gene by using the plasmid pIG121-CP ($Kin^-$), pIG121-VP3/GFP was additionally introduced. The transformed plant integrated with the polyhedrin gene alone was hygromycin-resistant but kanamycin-sensitive. As a result of subsequent introduction of pIG121-VP3/GFP, the transformed plant became sensitive also to hygromycin. Through this two-step screening, the transformed plant cells having both the polyhedrin gene and the VP3/GFP chimeric gene was finally obtained.

Host Plants Used for Transformation

Potato (Family Solanaceae) cultured under aseptic conditions was used in the experiment, but the plant is not restricted to this plant. The above-mentioned vector is for agrobacterium, and the promoter used was CaMV35S. Dicotyledons such as plants belonging to the family Solanaceae are generally used as the hosts into which genes can be introduced, but monocotyledons may be used.

Experimental Example 3

Purification of Polyhedra

Transformed plant cells having both the polyhedrin gene and the VP3/GFP chimeric gene were homogenized to release polyhedra from cells. The homogenate was washed with 1% Tween 20, and polyhedra was harvested by centrifugation. Then centrifugation at 50,000×g for 45 minutes with the sucrose density gradient from I 0.5M to 2.2 M was performed to separate the fraction of polyhedra. The fraction was washed with PBS, and centrifuged at 15,000×g for 10 minutes, to give purified polyhedra.

Measurement of Fluorescence of VP3/GFP

It is known that GFP is stable at a pH between 5 and 12, and polyhedra is dissolved at a pH exceeding 10.0. Then fluorescence from GFP was measured before and after dissolution of polyhedra to determine whether VP3 was occluded in polyhedra. Polyhedra, after purification, was suspended in I ml each of distilled water, 50 mM acetate buffer (pH4.0), and 5 mM carbonate-bicarbonate buffer (pH 1.0). The pH of the suspension in the acetate buffer was gradually elevated by addition of the 5N-NaOH solution, and the suspension was incubated at 300C for 30 minutes when pH became 6.0, 10.0, and 12.5. Then the fluorescence from GFP was excited at 475 nm and measured at 510 nm with the F-2000 Fluorescence Spectrophotometer (HITACHI). The amount of protein was determined with the Lowry's method and fluorescency per mg of the protein was calculated.

Results of Measurement of Fluorescence of VP3/GFP

Formation of polyhedra from the transformed plant cells into which the polyhedrin gene and the VP3/GFP chimeric gene had been introduced was confirmed. Thus it was confirmed that polyhedrin was expressed and it formed the structure polyhedra in plant cells as well as in insect cells, as was previously analogized from the homology between BmCPV and other plant viruses. Then polyhedra was purified from the plant tissue, and when the purified polyhedra was suspended in water, green fluorescence was noted (FIG. 7). This indicates that VP3/GFP is expressed also in plant cells as in insect cells, and exhibits its properties as a functional protein. This indicates also that a part of VP3/GFP is exposed on the surface of polyhedra.

Purified polyhedra was suspended in the acetate buffer (pH4.0) so that VP3/GFP exposed on the surface of polyhedra might become unable to emit green fluorescence, and then green fluorescence that became dissolved from polyhedra with gradual increase of pH was measured. At pH 10.0 or a lower pH, no change was noted in green fluorescence, though at a pH exceeding 10.0, polyhedra was dissolved and an intense green fluorescence was noted (FIG. 7). This indicated that the VP3-GFP fusion protein was occluded in polyhedra and became dissolved along with dissolution of polyhedra. That is, also in plant cells, polyhedrin of BmCPV and VP3 identify each other through their specific interaction, and therefore the VP3-GFP fusion protein (one of the Examples of the objective proteins of the invention) was occluded in particulates called polyhedra.

INDUSTRIAL APPLICABILITY

This invention provides protein-embedded crystals where various unstable functional proteins in the form of micro crystals are occluded in the stable cytoplasmic polyhedrin crystals. Therefore this invention makes it possible to store extremely unstable enzymes over a long time and to control expression of the function of a functional protein in a stage-specific manner. In addition, a functional protein incorporated in particulates can be used as a nucleus for crystallization of a protein, a process necessary for analysis of the higher-order structure of the protein, because the particulates are crystal-like. Furthermore, crystallized proteins are expected to be used as device materials including electronic materials and optical materials based on their physical properties.

As explained in detail, the invention that has been applied for patent provides a method for occlusion of a objective protein with the viral occlusion body protein in plants, and a method for preparing particulates where an objective protein is occluded with the viral occlusion body protein in plants. The invention makes it possible to produce a large amount of particulates that have incorporated an objective protein without any virus occluded. Incorporation into particulates makes it kpossible to store extremely unstable enzymes over an extended period of time and to control expression of the function of a functional protein in a stage-specific manner. In addition, an objective protein incorporated in particulates to crystallization of the protein, a process necessary for analysis of the higher-order structure of the protein, because the particulates are crystal-like.

The invention claimed is:

1. A protein complex having a structure that a heterologous target protein is occluded with a viral occlusion body protein encoded by nucleic acids of cytoplasmic polyhedrosis virus (CPV), wherein the target protein is fused to the C-terminus of SEQ ID NO:2, and wherein the target protein is occluded within the *Bombyx mori* CPV strain H polyhedrin.

2. The protein complex according to claim 1, wherein the occlusion body protein contributes to improvement of stability or protection, or improvement of preservability, or a combination thereof, of the target protein.

3. The protein complex according to claim 1 or 2, wherein the complex is produced in particulates.

4. The protein complex according to claim 1 or 2, wherein the complex is produced by incorporation of the target protein in a crystalline form during crystallization of the occlusion body protein.

5. The protein complex according to claim 1 or 2, wherein the protein complex is produced in insect cells.

6. The protein complex according to claim 1 or 2, wherein the target protein is selected from the group consisting of: proteins that fluoresce due to ultraviolet light, enzymes, immune antibody proteins, proteins having chromophores, and proteins having light absorbing groups.

7. A method for producing in cells a protein complex according to claim 1 having a structure that a heterologous target protein is occluded with the viral occlusion body protein encoded by nucleic acids of cytoplasmic polyhedrosis virus, comprising providing in the cells the target protein fused to the C-terminus of SEQ ID NO:2, and wherein the target protein is occluded within the *Bombyx mori* CPV strain H polyhedrin, wherein the providing step comprises:

transforming the cells with a virus vector that has been integrated with a DNA encoding the target protein together with a virus vector that has been integrated with a DNA encoding the viral occlusion body protein, and culturing the transformed cells so as to produce the protein complex.

8. The method according to claim 7, wherein the protein complex is produced in insect cells.

9. The method according to claim 7 or 8, wherein the target protein is selected from the group consisting of proteins that fluoresce due to ultraviolet light, enzymes, immune antibody proteins, proteins having chromophores, and proteins having light absorbing groups.

* * * * *

```
                              SEQUENCE LISTING

<160> NUMBER OF SEQ ID NOS: 4

<210> SEQ ID NO 1
<211> LENGTH: 3259
<212> TYPE: DNA
<213> ORGANISM: Cypovirus
<220> FEATURE:
<221> NAME/KEY: CDS
<222> LOCATION: (14)..(3187)

<400> SEQUENCE: 1
agtaatttcc acc atg tgg cat tat acg agt atc aac aat gac acg aga       49
               Met Trp His Tyr Thr Ser Ile Asn Asn Asp Thr Arg
               1               5                   10 gta gca ctt gac ccc aaa ccg aat caa att aga acg ata aca aaa cca      97
Val Ala Leu Asp Pro Lys Pro Asn Gln Ile Arg Thr Ile Thr Lys Pro
        15                  20                  25 aac aca gta cct caa ctc ggc aca gac tat ttg tat act ttc aac tca     145
Asn Thr Val Pro Gln Leu Gly Thr Asp Tyr Leu Tyr Thr Phe Asn Ser
    30                  35                  40 caa cga cga tca cac acg tta cga cta cta ggg cct ttt cag tac ttc     193
Gln Arg Arg Ser His Thr Leu Arg Leu Leu Gly Pro Phe Gln Tyr Phe
 45                  50                  55                  60 aac ttc tcc gag aca gat aga gga cat cca tta ttt cgc cta cct ctt     241
Asn Phe Ser Glu Thr Asp Arg Gly His Pro Leu Phe Arg Leu Pro Leu
                65                  70                  75 aag tat cca tca aaa gca ata cca gca gat gag tta att gac aat tta     289
Lys Tyr Pro Ser Lys Ala Ile Pro Ala Asp Glu Leu Ile Asp Asn Leu
            80                  85                  90 cac tca tgg atg cgt tca gtt cat cta tta cac gta cgc tcg gaa gac     337
His Ser Trp Met Arg Ser Val His Leu Leu His Val Arg Ser Glu Asp
        95                 100                 105 aac acg cta cgt tac aac tgg atg tta ggt gtg tac gcg cgc tca act     385
Asn Thr Leu Arg Tyr Asn Trp Met Leu Gly Val Tyr Ala Arg Ser Thr
```

```
                 110                 115                 120
aat tac act aca cca gtc gga cag ttg gta gtt aat gcg cca gcg att      433
Asn Tyr Thr Thr Pro Val Gly Gln Leu Val Val Asn Ala Pro Ala Ile
125                 130                 135                 140 ctc aac tat tct aat ccg caa gat gca ttc aat agt gta ttt gta gcg      481
Leu Asn Tyr Ser Asn Pro Gln Asp Ala Phe Asn Ser Val Phe Val Ala
                145                 150                 155 tta ggt ata gac tac att gat ata ccg ata act aac agc aac atc ttt      529
Leu Gly Ile Asp Tyr Ile Asp Ile Pro Ile Thr Asn Ser Asn Ile Phe
                    160                 165                 170 gac gac agt tcg aca ccc tat aat gtt cgt att tgg cat gcc cct act      577
Asp Asp Ser Ser Thr Pro Tyr Asn Val Arg Ile Trp His Ala Pro Thr
                175                 180                 185 atg acg gag gtt aac cat atc ctt gcg cta atg cga aag agt aca ctg      625
Met Thr Glu Val Asn His Ile Leu Ala Leu Met Arg Lys Ser Thr Leu
190                 195                 200 gta tca aca cat tca tct tgg cat tgg gat gta tta cat acg ttt cac      673
Val Ser Thr His Ser Ser Trp His Trp Asp Val Leu His Thr Phe His
205                 210                 215                 220 tat agg agc gaa tca gat atg atc gat cac ttt gcg gct aag ata ctg      721
Tyr Arg Ser Glu Ser Asp Met Ile Asp His Phe Ala Ala Lys Ile Leu
                    225                 230                 235 gaa gat tgg cga cag aaa gag aaa ctt gat aag ggc gca tta gtc gag      769
Glu Asp Trp Arg Gln Lys Glu Lys Leu Asp Lys Gly Ala Leu Val Glu
                240                 245                 250 gct gat aga gtg gtt caa aga cta ata cca ttg agc tct tca aca tat      817
Ala Asp Arg Val Val Gln Arg Leu Ile Pro Leu Ser Ser Ser Thr Tyr
                255                 260                 265 gtg cag cgt tta gca gcg atc ggc gcg tta tat ccc aat gaa ttc acc      865
Val Gln Arg Leu Ala Ala Ile Gly Ala Leu Tyr Pro Asn Glu Phe Thr
270                 275                 280 gag aat gta ttg gac ttg agc aga ctt tca aca gca tta ttg caa cta      913
Glu Asn Val Leu Asp Leu Ser Arg Leu Ser Thr Ala Leu Leu Gln Leu
285                 290                 295                 300 tca gat acg tac tat caa cat gca aat gat caa ctc aga cgt tta tat      961
Ser Asp Thr Tyr Tyr Gln His Ala Asn Asp Gln Leu Arg Arg Leu Tyr
                    305                 310                 315 aga cgt atg tat aac gac tca agg acg ttg tat atg aca caa aga cat     1009
Arg Arg Met Tyr Asn Asp Ser Arg Thr Leu Tyr Met Thr Gln Arg His
                320                 325                 330 cag gag cta ctg cta gca caa ata act gcc gat ccg aat ata ctt tta     1057
Gln Glu Leu Leu Leu Ala Gln Ile Thr Ala Asp Pro Asn Ile Leu Leu
                335                 340                 345 tat cca tat aca tac ata ttt aca act gcg tat act tct atg aac tat     1105
Tyr Pro Tyr Thr Tyr Ile Phe Thr Thr Ala Tyr Thr Ser Met Asn Tyr
350                 355                 360 atc tcc aat aca ggg caa ggc cgt ata aag cat tca cta gct gtt act     1153
Ile Ser Asn Thr Gly Gln Gly Arg Ile Lys His Ser Leu Ala Val Thr
365                 370                 375                 380 gga aca act gag cat act ata gca gac ata aca ttg ggt cca atg agt     1201
Gly Thr Thr Glu His Thr Ile Ala Asp Ile Thr Leu Gly Pro Met Ser
                385                 390                 395 gag gat gta gtt acc ata tct atg gtc gag cca atg agc ata gct gcg     1249
Glu Asp Val Val Thr Ile Ser Met Val Glu Pro Met Ser Ile Ala Ala
                400                 405                 410 gag gat atg tat gga tac gtg ctt gat acg ccg aca cgt gac atc tgg     1297
Glu Asp Met Tyr Gly Tyr Val Leu Asp Thr Pro Thr Arg Asp Ile Trp
                415                 420                 425 cca gcg gac gaa cag ata gag caa aag gga gac gcg gtc gct ttg tat     1345
```

-continued

```
Pro Ala Asp Glu Gln Ile Glu Gln Lys Gly Asp Ala Val Ala Leu Tyr
    430                 435                 440 gat aca aaa aca tct aga gca ctg ggc atg ttc aac aac act gta cgt    1393
Asp Thr Lys Thr Ser Arg Ala Leu Gly Met Phe Asn Asn Thr Val Arg
445                 450                 455                 460 att gac gac ttg ttg tct ccg cta tta ggc ctg gtt tac aga acg tac    1441
Ile Asp Asp Leu Leu Ser Pro Leu Leu Gly Leu Val Tyr Arg Thr Tyr
                465                 470                 475 att aaa ggc gat aca atg act atg acc cag ggc agt ttg gat cac cta    1489
Ile Lys Gly Asp Thr Met Thr Met Thr Gln Gly Ser Leu Asp His Leu
                480                 485                 490 act tta tgt gca gca gtt gat tca gac atc act ttt gtg ggt aac agg    1537
Thr Leu Cys Ala Ala Val Asp Ser Asp Ile Thr Phe Val Gly Asn Arg
            495                 500                 505 atg ata gcg cca ttg gca gag gga tat ata ccc aaa gcg atg cat cgg    1585
Met Ile Ala Pro Leu Ala Glu Gly Tyr Ile Pro Lys Ala Met His Arg
        510                 515                 520 aat aat tca acg atg aaa atg ctc agt tta tac gtg gca ttg aaa aag    1633
Asn Asn Ser Thr Met Lys Met Leu Ser Leu Tyr Val Ala Leu Lys Lys
525                 530                 535                 540 tta gaa aat ttt aca acc aat tca tat cta atg gct ccg gat aca tcc    1681
Leu Glu Asn Phe Thr Thr Asn Ser Tyr Leu Met Ala Pro Asp Thr Ser
                545                 550                 555 att atc ttg ctc ggt gca gag aga gaa ccc gct gta agt ata ttg cga    1729
Ile Ile Leu Leu Gly Ala Glu Arg Glu Pro Ala Val Ser Ile Leu Arg
                560                 565                 570 aga ttt aat cgt agc gtt tct aat gta cgc ata atc gga atg gga gac    1777
Arg Phe Asn Arg Ser Val Ser Asn Val Arg Ile Ile Gly Met Gly Asp
            575                 580                 585 aga gca gtc gag cct aac att agg gtt cgt gtg cca ttc cct ata gat    1825
Arg Ala Val Glu Pro Asn Ile Arg Val Arg Val Pro Phe Pro Ile Asp
        590                 595                 600 aaa aac atc tcg gct gat ttc atc ata tgt gat att aac tcc tat gag    1873
Lys Asn Ile Ser Ala Asp Phe Ile Ile Cys Asp Ile Asn Ser Tyr Glu
605                 610                 615                 620 gac cag agt ttt gag tcc atg ttc ggt gag act ata tcg gta gtg act    1921
Asp Gln Ser Phe Glu Ser Met Phe Gly Glu Thr Ile Ser Val Val Thr
                625                 630                 635 aca tgc gct agc gcc gcg aca cgt gta ctt gtg aag att aat cat cca    1969
Thr Cys Ala Ser Ala Ala Thr Arg Val Leu Val Lys Ile Asn His Pro
            640                 645                 650 tct gaa tat atg ata aac agt gta att gag cgg cta tca caa ttg gga    2017
Ser Glu Tyr Met Ile Asn Ser Val Ile Glu Arg Leu Ser Gln Leu Gly
        655                 660                 665 ggt gtg ttt tat cac act gca cta ctg aag aca gct tcg cag aac cca    2065
Gly Val Phe Tyr His Thr Ala Leu Leu Lys Thr Ala Ser Gln Asn Pro
    670                 675                 680 tac tca tac gaa aca tat atc tac att aca cct ata gct gcg gca gtt    2113
Tyr Ser Tyr Glu Thr Tyr Ile Tyr Ile Thr Pro Ile Ala Ala Ala Val
685                 690                 695                 700 agg ttc ccc ttt tac agc aac tct gct ata att aat aga tac atg act    2161
Arg Phe Pro Phe Tyr Ser Asn Ser Ala Ile Ile Asn Arg Tyr Met Thr
                705                 710                 715 gca gtg gca gat gat gag acg cct ata att ccc agc atc cat aca gtt    2209
Ala Val Ala Asp Asp Glu Thr Pro Ile Ile Pro Ser Ile His Thr Val
            720                 725                 730 att aag ggg cat agt aac aca tac tca cct ggt ttg ttc tgt gga tgt    2257
Ile Lys Gly His Ser Asn Thr Tyr Ser Pro Gly Leu Phe Cys Gly Cys
        735                 740                 745
```

```
att gac gta caa tcg gcg cca ttc gca ctt tca cag cta aaa tcc tat      2305
Ile Asp Val Gln Ser Ala Pro Phe Ala Leu Ser Gln Leu Lys Ser Tyr
    750                 755                 760 tgc tca gaa gcg aca acc tgg cgc gtt gac agt gac gat aac tta gtt      2353
Cys Ser Glu Ala Thr Thr Trp Arg Val Asp Ser Asp Asp Asn Leu Val
765                 770                 775                 780 aac atc att gcc aga att gat ccc gcg cgt ata gct ttg gaa ttt cga      2401
Asn Ile Ile Ala Arg Ile Asp Pro Ala Arg Ile Ala Leu Glu Phe Arg
                785                 790                 795 aca cgc tca aat act agc gcc tat cat gaa tac caa cgc tat gta cca      2449
Thr Arg Ser Asn Thr Ser Ala Tyr His Glu Tyr Gln Arg Tyr Val Pro
                    800                 805                 810 aat gga ctc ggc ttt aaa ggg cgg aag acg cga gag ttt agg tat ata      2497
Asn Gly Leu Gly Phe Lys Gly Arg Lys Thr Arg Glu Phe Arg Tyr Ile
                815                 820                 825 cat cgt gag gta aca ttt ata cat aaa ctg atg aca tat gct tta ata      2545
His Arg Glu Val Thr Phe Ile His Lys Leu Met Thr Tyr Ala Leu Ile
    830                 835                 840 cga gag cag ata tca tta act gaa aac atg act caa gtg gta agt att      2593
Arg Glu Gln Ile Ser Leu Thr Glu Asn Met Thr Gln Val Val Ser Ile
845                 850                 855                 860 ggc ggc cgt aac ctc gct gat ata tct gtc gtc cct ctt aat atg aaa      2641
Gly Gly Arg Asn Leu Ala Asp Ile Ser Val Val Pro Leu Asn Met Lys
                865                 870                 875 tac gtg gtg ata gac cca gcc aca cgt atc gaa acg tta acg cag gaa      2689
Tyr Val Val Ile Asp Pro Ala Thr Arg Ile Glu Thr Leu Thr Gln Glu
                    880                 885                 890 aag aag aat att gaa gta caa tct aga cca ttc tca ttt gat gcg gca      2737
Lys Lys Asn Ile Glu Val Gln Ser Arg Pro Phe Ser Phe Asp Ala Ala
                895                 900                 905 agc atg gat tta gag aat aat tct ata tat cta ttt atc gca gta atc      2785
Ser Met Asp Leu Glu Asn Asn Ser Ile Tyr Leu Phe Ile Ala Val Ile
    910                 915                 920 atg aat gaa cca aat gga gca gct act ccc gcc aga acg caa atg gat      2833
Met Asn Glu Pro Asn Gly Ala Ala Thr Pro Ala Arg Thr Gln Met Asp
925                 930                 935                 940 aag ata cgt aat gtt gcc aca gct atg cta acc agg act aac tgc gtc      2881
Lys Ile Arg Asn Val Ala Thr Ala Met Leu Thr Arg Thr Asn Cys Val
                945                 950                 955 gca tac att tcg ttt tac gag gca ggg ata atc aca aga ttg gat caa      2929
Ala Tyr Ile Ser Phe Tyr Glu Ala Gly Ile Ile Thr Arg Leu Asp Gln
                    960                 965                 970 tca acc gcg cat aag act ata cgt gtt gaa gaa ggt cga ctg aaa gtg      2977
Ser Thr Ala His Lys Thr Ile Arg Val Glu Glu Gly Arg Leu Lys Val
                975                 980                 985 gca aat tat gta ccc gtg gat acg ctc gtt gaa gca gac gtg acg ttg      3025
Ala Asn Tyr Val Pro Val Asp Thr Leu Val Glu Ala Asp Val Thr Leu
    990                 995                 1000 atg tta cgc gat atc ggc ata aca cat gag ata ata aga cca tcg acg      3073
Met Leu Arg Asp Ile Gly Ile Thr His Glu Ile Ile Arg Pro Ser Thr
1005                1010                1015                1020 cct gaa ctc ata aat gcc tgt tca aac tat ggc att cgc cta ggt tcg      3121
Pro Glu Leu Ile Asn Ala Cys Ser Asn Tyr Gly Ile Arg Leu Gly Ser
                1025                1030                1035 aca ggt ggc gcg gtt ttg gac gtg ttc aat cac tac tct ccc gtg atc      3169
Thr Gly Gly Ala Val Leu Asp Val Phe Asn His Tyr Ser Pro Val Ile
                    1040                1045                1050 aaa ctt gta cgc tcg taa tgctgagtct taaccacagg agttgaggag             3217
Lys Leu Val Arg Ser
        1055
```

```
ctctgtcccg ggagggacac tgtggggtgg gaaacgttag cc         3259
```

<210> SEQ ID NO 2
<211> LENGTH: 1057
<212> TYPE: PRT
<213> ORGANISM: Cypovirus

<400> SEQUENCE: 2

```
Met Trp His Tyr Thr Ser Ile Asn Asn Asp Thr Arg Val Ala Leu Asp
1               5                   10                  15

Pro Lys Pro Asn Gln Ile Arg Thr Ile Thr Lys Pro Asn Thr Val Pro
            20                  25                  30

Gln Leu Gly Thr Asp Tyr Leu Tyr Thr Phe Asn Ser Gln Arg Arg Ser
        35                  40                  45

His Thr Leu Arg Leu Leu Gly Pro Phe Gln Tyr Phe Asn Phe Ser Glu
    50                  55                  60

Thr Asp Arg Gly His Pro Leu Phe Arg Leu Pro Lys Tyr Pro Ser
65                  70                  75                  80

Lys Ala Ile Pro Ala Asp Glu Leu Ile Asp Asn Leu His Ser Trp Met
                85                  90                  95

Arg Ser Val His Leu Leu His Val Arg Ser Glu Asp Asn Thr Leu Arg
            100                 105                 110

Tyr Asn Trp Met Leu Gly Val Tyr Ala Arg Ser Thr Asn Tyr Thr Thr
        115                 120                 125

Pro Val Gly Gln Leu Val Val Asn Ala Pro Ala Ile Leu Asn Tyr Ser
    130                 135                 140

Asn Pro Gln Asp Ala Phe Asn Ser Val Phe Val Ala Leu Gly Ile Asp
145                 150                 155                 160

Tyr Ile Asp Ile Pro Ile Thr Asn Ser Asn Ile Phe Asp Asp Ser Ser
                165                 170                 175

Thr Pro Tyr Asn Val Arg Ile Trp His Ala Pro Thr Met Thr Glu Val
            180                 185                 190

Asn His Ile Leu Ala Leu Met Arg Lys Ser Thr Leu Val Ser Thr His
        195                 200                 205

Ser Ser Trp His Trp Asp Val Leu His Thr Phe His Tyr Arg Ser Glu
    210                 215                 220

Ser Asp Met Ile Asp His Phe Ala Ala Lys Ile Leu Glu Asp Trp Arg
225                 230                 235                 240

Gln Lys Glu Lys Leu Asp Lys Gly Ala Leu Val Glu Ala Asp Arg Val
                245                 250                 255

Val Gln Arg Leu Ile Pro Leu Ser Ser Ser Thr Tyr Val Gln Arg Leu
            260                 265                 270

Ala Ala Ile Gly Ala Leu Tyr Pro Asn Glu Phe Thr Glu Asn Val Leu
        275                 280                 285

Asp Leu Ser Arg Leu Ser Thr Ala Leu Leu Gln Leu Ser Asp Thr Tyr
    290                 295                 300

Tyr Gln His Ala Asn Asp Gln Leu Arg Arg Leu Tyr Arg Arg Met Tyr
305                 310                 315                 320

Asn Asp Ser Arg Thr Leu Tyr Met Thr Gln Arg His Gln Glu Leu Leu
                325                 330                 335

Leu Ala Gln Ile Thr Ala Asp Pro Asn Ile Leu Leu Tyr Pro Tyr Thr
            340                 345                 350

Tyr Ile Phe Thr Thr Ala Tyr Ser Met Asn Tyr Ile Ser Asn Thr
        355                 360                 365
```

```
Gly Gln Gly Arg Ile Lys His Ser Leu Ala Val Thr Gly Thr Thr Glu
    370                 375                 380

His Thr Ile Ala Asp Ile Thr Leu Gly Pro Met Ser Glu Asp Val Val
385                 390                 395                 400

Thr Ile Ser Met Val Glu Pro Met Ser Ile Ala Ala Glu Asp Met Tyr
                405                 410                 415

Gly Tyr Val Leu Asp Thr Pro Thr Arg Asp Ile Trp Pro Ala Asp Glu
            420                 425                 430

Gln Ile Glu Gln Lys Gly Asp Ala Val Ala Leu Tyr Asp Thr Lys Thr
        435                 440                 445

Ser Arg Ala Leu Gly Met Phe Asn Asn Thr Val Arg Ile Asp Asp Leu
    450                 455                 460

Leu Ser Pro Leu Leu Gly Leu Val Tyr Arg Thr Tyr Ile Lys Gly Asp
465                 470                 475                 480

Thr Met Thr Met Thr Gln Gly Ser Leu Asp His Leu Thr Leu Cys Ala
                485                 490                 495

Ala Val Asp Ser Asp Ile Thr Phe Val Gly Asn Arg Met Ile Ala Pro
            500                 505                 510

Leu Ala Glu Gly Tyr Ile Pro Lys Ala Met His Arg Asn Asn Ser Thr
        515                 520                 525

Met Lys Met Leu Ser Leu Tyr Val Ala Leu Lys Lys Leu Glu Asn Phe
    530                 535                 540

Thr Thr Asn Ser Tyr Leu Met Ala Pro Asp Thr Ser Ile Ile Leu Leu
545                 550                 555                 560

Gly Ala Glu Arg Glu Pro Ala Val Ser Ile Leu Arg Arg Phe Asn Arg
                565                 570                 575

Ser Val Ser Asn Val Arg Ile Ile Gly Met Gly Asp Arg Ala Val Glu
            580                 585                 590

Pro Asn Ile Arg Val Arg Val Pro Phe Pro Ile Asp Lys Asn Ile Ser
        595                 600                 605

Ala Asp Phe Ile Ile Cys Asp Ile Asn Ser Tyr Glu Asp Gln Ser Phe
    610                 615                 620

Glu Ser Met Phe Gly Glu Thr Ile Ser Val Val Thr Thr Cys Ala Ser
625                 630                 635                 640

Ala Ala Thr Arg Val Leu Val Lys Ile Asn His Pro Ser Glu Tyr Met
                645                 650                 655

Ile Asn Ser Val Ile Glu Arg Leu Ser Gln Leu Gly Gly Val Phe Tyr
            660                 665                 670

His Thr Ala Leu Leu Lys Thr Ala Ser Gln Asn Pro Tyr Ser Tyr Glu
        675                 680                 685

Thr Tyr Ile Tyr Ile Thr Pro Ile Ala Ala Ala Val Arg Phe Pro Phe
    690                 695                 700

Tyr Ser Asn Ser Ala Ile Ile Asn Arg Tyr Met Thr Ala Val Ala Asp
705                 710                 715                 720

Asp Glu Thr Pro Ile Ile Pro Ser Ile His Thr Val Ile Lys Gly His
                725                 730                 735

Ser Asn Thr Tyr Ser Pro Gly Leu Phe Cys Gly Cys Ile Asp Val Gln
            740                 745                 750

Ser Ala Pro Phe Ala Leu Ser Gln Leu Lys Ser Tyr Cys Ser Glu Ala
        755                 760                 765

Thr Thr Trp Arg Val Asp Ser Asp Asp Asn Leu Val Asn Ile Ile Ala
    770                 775                 780
```

```
Arg Ile Asp Pro Ala Arg Ile Ala Leu Glu Phe Arg Thr Arg Ser Asn
785                 790                 795                 800

Thr Ser Ala Tyr His Glu Tyr Gln Arg Tyr Val Pro Asn Gly Leu Gly
            805                 810                 815

Phe Lys Gly Arg Lys Thr Arg Glu Phe Arg Tyr Ile His Arg Glu Val
            820                 825                 830

Thr Phe Ile His Lys Leu Met Thr Tyr Ala Leu Ile Arg Glu Gln Ile
        835                 840                 845

Ser Leu Thr Glu Asn Met Thr Gln Val Val Ser Ile Gly Gly Arg Asn
850                 855                 860

Leu Ala Asp Ile Ser Val Val Pro Leu Asn Met Lys Tyr Val Val Ile
865                 870                 875                 880

Asp Pro Ala Thr Arg Ile Glu Thr Leu Thr Gln Glu Lys Lys Asn Ile
            885                 890                 895

Glu Val Gln Ser Arg Pro Phe Ser Phe Asp Ala Ala Ser Met Asp Leu
            900                 905                 910

Glu Asn Asn Ser Ile Tyr Leu Phe Ile Ala Val Ile Met Asn Glu Pro
            915                 920                 925

Asn Gly Ala Ala Thr Pro Ala Arg Thr Gln Met Asp Lys Ile Arg Asn
930                 935                 940

Val Ala Thr Ala Met Leu Thr Arg Thr Asn Cys Val Ala Tyr Ile Ser
945                 950                 955                 960

Phe Tyr Glu Ala Gly Ile Ile Thr Arg Leu Asp Gln Ser Thr Ala His
            965                 970                 975

Lys Thr Ile Arg Val Glu Glu Gly Arg Leu Lys Val Ala Asn Tyr Val
            980                 985                 990

Pro Val Asp Thr Leu Val Glu Ala Asp Val Thr Leu Met Leu Arg Asp
            995                 1000                1005

Ile Gly Ile Thr His Glu Ile Ile Arg Pro Ser Thr Pro Glu Leu Ile
    1010                1015                1020

Asn Ala Cys Ser Asn Tyr Gly Ile Arg Leu Gly Ser Thr Gly Gly Ala
1025                1030                1035                1040

Val Leu Asp Val Phe Asn His Tyr Ser Pro Val Ile Lys Leu Val Arg
                1045                1050                1055

Ser
```

<210> SEQ ID NO 3
<211> LENGTH: 28
<212> TYPE: DNA
<213> ORGANISM: Artificial Sequence
<220> FEATURE:
<223> OTHER INFORMATION: Artificial sequence with an addition of restriction enzyme NotI recognition site (gcggccgc) to 5' untranslated region of segment 4 from Bombyx mori cytoplasmic polyhedrosis virus

<400> SEQUENCE: 3
gatcgcggcc gcagtaattt ccaccatg                          28

<210> SEQ ID NO 4
<211> LENGTH: 23
<212> TYPE: DNA
<213> ORGANISM: Artificial Sequence
<220> FEATURE:
<223> OTHER INFORMATION: Artificial sequence with an addition of restriction enzyme BamHI recognition site (ggatcc) to 3' untranslated region of segment 4 from Bombyx mori cytoplasmic polyhedrosis virus 449

```
-continued

<400> SEQUENCE: 4
gatcggatcc ggctaacgtt tcc                                    23
```